(12) United States Patent
Nakaki et al.

(10) Patent No.: US 8,551,711 B2
(45) Date of Patent: Oct. 8, 2013

(54) SCREENING METHOD OF GLUTATHIONE-INCREASING SUBSTANCE

(75) Inventors: Toshio Nakaki, Saitama (JP); Masahiko Watabe, Saitama (JP); Koji Aoyama, Tokyo (JP)

(73) Assignee: Teikyo University, Tokyo (JP)

( * ) Notice: Subject to any disclaimer, the term of this patent is extended or adjusted under 35 U.S.C. 154(b) by 988 days.

(21) Appl. No.: 12/226,869

(22) PCT Filed: Apr. 26, 2007

(86) PCT No.: PCT/JP2007/059104
§ 371 (c)(1),
(2), (4) Date: Jan. 30, 2009

(87) PCT Pub. No.: WO2007/129598
PCT Pub. Date: Nov. 15, 2007

(65) Prior Publication Data
US 2009/0162886 A1    Jun. 25, 2009

(30) Foreign Application Priority Data
May 2, 2006   (JP) ................................. 2006-128369

(51) Int. Cl.
*C12Q 1/68* (2006.01)
*G01N 33/567* (2006.01)

(52) U.S. Cl.
USPC .......................... 435/6.17; 435/7.21; 435/7.8

(58) Field of Classification Search
None
See application file for complete search history.

(56) References Cited

U.S. PATENT DOCUMENTS 6,808,893 B1 * 10/2004 Rothstein et al. ............ 435/69.1

OTHER PUBLICATIONS

Watabe et al. Teikyo Igaku Zasshi 29(4):227-230 Jul. 4, 2006.*
Aoyama et al. Nature Neuroscience 9:119-126 Jan. 2006 (published online Nov. 27, 2005.*
Bendahan et al. JBC, 275:37436-37442, 2000.*
M. Watabe et al., "A Dominant Role of GTRAP3-18 in Neuronal Glutathione Synthesis", The Journal of Neuroscience, vol. 28, No. 38, pp. 9404-9413, Sep. 17, 2008.
M. Watabe et al., "Regulation of Glutathione Synthesis via Interaction between Glutamate Transport-Associated Protein 3-18 (GTRAP3-18) and Excitatory Amino Acid Carrier-1 (EAAC1) at Plasma Membrane", Molecular Pharmacology, vol. 72, No. 5, pp. 1103-1110, 2007.

* cited by examiner

*Primary Examiner* — Oluwatosin Ogunbiyi
(74) *Attorney, Agent, or Firm* — Wenderoth, Lind & Ponack, L.L.P.

(57) ABSTRACT

As a means for treating diseases such as neurodegenerative diseases, malignant tumors and infectious diseases, a method for screening a substance increasing glutathione is provided. According to this method, by contacting a test substance with a cell expressing a GTRAP3-18 protein, a substance decreasing the amount of expression of the GTRAP3-18 protein or inhibiting a function of the GTRAP3-18 protein is specified as a target substance.

2 Claims, 7 Drawing Sheets

SCREENING METHOD OF GLUTATHIONE-INCREASING SUBSTANCE

This application is a U.S. national stage of International Application No. PCT/JP2007/059104 filed Apr. 26, 2007.

TECHNICAL FIELD

The invention of the present application relates to a method for screening a substance increasing the amount of intracellular glutathione which can make an active ingredient of a remedy of a number of diseases such as neurodegenerative diseases, malignant tumors and infectious diseases.

BACKGROUND ART

Intracellular glutathione is a main antioxidant of an organism and is an extremely important molecule for biophylaxis (Non-Patent Document 1). Glutathione is constituted of three amino acids (glycine, cysteine and glutamic acid) and is synthesized by a two-stage enzymatic reaction. But, since merely administration of the amino acids of three kinds as raw materials of glutathione does not increase glutathione in a cell, a complicated regulation mechanism is expected.

It is known that when glutathione in a nerve cell is experimentally decreased, neurodegeneration occurs (Non-Patent Document 2). In actual diseases, it is also known that glutathione decreases in a number of diseases such as neurodegenerative diseases (for example, Parkinson's disease and Alzheimer's disease), malignant tumors and infectious diseases. It is expected that if a remedy for increasing glutathione is available, such is quite useful, and realization thereof is desired (Non-Patent Documents 3 to 6). But, such a remedy does not exist.

EAAC1 (excitory amino acid carrier-1) is expressed on a cell membrane, and was discovered as a protein for uptaking glutamic acid into cells (glutamic acid transport protein). However, it is known that EAAC1 has a low ability as a glutamic acid transport protein and that other proteins (for example, GLT-1 and GLAST) are much more important as the glutamic acid transport protein (Non-Patent Documents 7 to 8). Thereafter, it was found out that EAAC1 has an ability to transport not only glutamic acid but also other amino acids including cysteine (Non-Patent Documents 9 to 11).

Furthermore, it was recently discovered that EAAC1 is a necessary protein for keeping the amount of intracellular glutathione (Non-Patent Document 12). It was presumed that the matter that EAAC1 has an ability to transport glutamic acid and cysteine, which are constituent amino acids of glutathione, contributes to this.

Accordingly, if a measure for activating EAAC1 is available, it may be theoretically possible to increase the amount of intracellular glutathione. However, molecules or compounds that bind with EAAC1 to activate it have not been discovered to date. Also, a point of concern about the development of drugs targeting EAAC1 is the fact that all of molecules and compounds binding with a transport protein on a cell membrane are inhibitors. For instance, there are examples including SSRI, an antidepressant for a serotonin transport protein; desipramine, an antidepressant for a noradrenaline transport protein; and reserpine, a depressor for an amine transport protein of nerve ending granules. Accordingly, it is thought that there is a high possibility that molecules or compounds targeting EAAC1 rather decrease the amount of glutathione, and actually, examples thereof exist (Non-Patent Document 13).

On the other hand, a protein referred to as GTRAP3-18 (glutamate-transporter-associated protein 3-18) as an in vivo molecule binding with EAAC1 exists. It is known that this GTRAP3-18 is often expressed in brain, spinal, kidney, heart and skeletal muscle and binds with EAAC1 to lower the transport ability of glutamic acid (Non-Patent Document 14). However, since the transport mechanism of EAAC1 is different in the respective amino acids (Non-Patent Documents 15 and 16), when GTRAP3-18 binds with EAAC1, how the transport ability of cysteine changes is unclear. Furthermore, how increase and decrease of GTRAP3-18 influence the amount of intracellular glutathione is quite unclear. An amino acid sequence of GTRAP3-18 and cDNA encoding GTRAP3-18 are described in Patent Document 1.

Patent Document 1: U.S. Pat. No. 6,808,893
Non-Patent Document 1: Dringen, Prog Neurobiol, 62: 649-671, 2000
Non-Patent Document 2: Jain et al., Proc Natl Acad Sci, 88: 1913-1917, 1991
Non-Patent Document 3: Exner et al., Wien Klin Wochenschr, 112: 610-616, 2000
Non-Patent Document 4: Lomaestro et al., Ann Pharmacother, 29: 1263-1273, 1995
Non-Patent Document 5: Reid and Johoor, Curr Opin Clin Nutr Metab Care, 4: 65-71, 2001
Non-Patent Document 6: Townsend and Tew, Oncogene, 22: 7369-7375, 2003
Non-Patent Document 7: Kanai et al., Neuroreport 6: 2357-2362, 1995
Non-Patent Document 8: Robinson and Dowd, Adv Pharmacol, 37: 69-115, 1997
Non-Patent Document 9: King, et al., Cardiovasc Res, 52: 84-94, 2001
Non-Patent Document 10: Chen and Swanson, J Neurochem, 84: 1332-1339, 2003
Non-Patent Document 11: Himi et al, J Neural Transm, 110: 1337-1348, 2003
Non-Patent Document 12: Aoyama et al., Nature Neuroscience, 9: 119-126, 2006
Non-Patent Document 13: Esslinger et al., Neuropharmacology, 49: 850-861, 2005
Non-Patent Document 14: Lin et al., Nature, 410: 84-88, 2001
Non-Patent Document 15: Bendahan, A. et al., J Biol Chem, 275: 37436-37442, 2000
Non-Patent Document 16: Borre and Kahner, J Biol Chem, 279: 2513-2519, 2004

DISCLOSURE OF INVENTION

As described above, the development of remedies increasing glutathione is desired as measures for a number of diseases such as neurodegenerative diseases, malignant tumors and infectious diseases.

A problem of the invention of the present application is to provide a means for screening a substance, which makes an active ingredient of a remedy for increasing glutathione.

The inventors of the present application paid attention to a GTRAP3-18 protein and made extensive and intensive investigations. As a result, it has been found that when the expression of the GTRAP3-18 protein is artificially decreased, the amount of glutathione increases, whereas when the expression of the GTRAP3-18 protein is increased, the amount of glutathione decreases.

The invention of the present application is made on the basis of such novel knowledge of the inventors.

That is, the invention of the present application is a method for screening a substance increasing the amount of intracellular glutathione, which comprises contacting a test substance with a cell expressing a GTRAP3-18 protein, thereby specifying a substance decreasing the amount of expression of the GTRAP3-18 protein or inhibiting a function of the GTRAP3-18 protein as a target substance.

The method of the present invention can also be performed for cells in an animal individual.

According to the present invention, it becomes possible to specify a substance capable of increasing the amount of intracellular glutathione, which substance has hitherto not existed at all. Such a substance largely promotes the development of a new remedy for diseases such as neurodegenerative diseases, malignant tumors and infectious diseases.

In the invention of the present application, the terms "decrease of the amount of expression of the GTRAP3-18 protein" mean a decrease of the GTRAP3-18 protein itself in a cell, a decrease of the amount of transcription of a gene encoding the GTRAP3-18 protein, a decrease of the amount of translation of from a gene transcription product to the GTRAP3-18 protein, or the like. Also, the terms "inhibition of a function of the GTRAP3-18 protein" mean that a function of the GTRAP3-18 protein (for example, a function to inhibit the EAAC1 activity and a function to decrease the amount of glutathione by inhibition of the EAAC1 activity) is inhibited. Furthermore, the terms "contacting a test substance with a cell" mean that a test substance is contacted with a cell such that the test substance acts on the expression of the GTRAP3-18 protein in the cell.

Other terms and concepts in this invention are defined in detail in the description of the embodiments of the invention and the working examples. Various technologies used for the purpose of carrying out this invention can be easily and surely carried out by those skilled in the art on the basis of known documents and the like exclusive of technologies whose sources have been elucidated specifically. For example, the genetic engineering and molecular biology technologies can be carried out on the basis of Sambrook and Maniatis, in Molecular Cloning: A Laboratory Manual, Gold Spring Harbor Laboratory Press, New York, 1989; Ausubel, F. M. et al., Current Protocols in Molecular Biology, John Wiley & Sons, New York, N.Y., 1995; and the like, or references cited in these documents.

BEST MODES FOR CARRYING OUT THE INVENTION

The "cell expressing a GTRAP3-18 protein" is a cell obtained by isolating such cell from an animal body and culturing it, or a cell in an animal body. A cultured cell is used for in vitro screening, whereas a cell in an animal body is for in vivo screening. An especially preferable cell is one expressing a large amount of the GTRAP3-18 protein, such as cell derived from brain, spinal, kidney, heart, skeletal muscle, or the like.

For in vitro screening, in particular, it is also possible to use a cell transformed by polynucleotide (cDNA) encoding the GTRAP3-18 protein. The cDNA can be isolated from a genome DNA library or a cDNA library using, as a probe, DNA fragments of a known nucleotide sequence or a partial sequence thereof. The obtained cDNA can be amplified by a usually employed genetic amplification method, for example, a PCR (polymerase chain reaction) method, an NASBN (nucleic acid sequence based amplification) method, a TMA (transcription-mediated amplification) method, and an SDA (strand displacement amplification) method. The cDNA can also be obtained by an RT-PCR method using mRNA isolated from a cell and primers synthesized on the basis of a known sequence. The cDNA sequence of human GTRAP3-18 is disclosed in Patent Document 1 (U.S. Pat. No. 6,808,893). Though the cell to be transformed is preferably a mammalian cell derived from a human being or the like, so far as it is aimed to confirm an effect of a test substance on the amount of expression of GTRAP3-18, cells of other animals and plants and prokaryotic cells such as Escherichia coli may also be employed.

In the case of in vitro screening, a test substance is added to a medium of cell culture, thereby contacting the test substance with the cell. In the case of in vivo screening, an animal is administered with a test substance (by, for example, oral administration, intravenous injection, intraperitoneal injection, subcutaneous injection and intracerebral injection), thereby contacting the test substance with a cell which expresses a large amount of the GTRAP3-18 protein, for example, those of brain, spinal, kidney, heart, skeletal muscle, or the like.

Examples of a test substance include organic or inorganic compounds (especially compounds with a low molecular weight), proteins and peptides. These substances may be ones whose functions and structures are known or unknown.

A "combinatorial chemical library" is a means effective as a group of test substances for efficiently specifying a target substance. The combinatorial chemical library is a collection of various chemical compositions formed by binding a number of chemical "building blocks" such as reagents by chemical synthesis or biological synthesis. For example, a linear combinatorial chemical library such as a peptide library is formed by setting building blocks (amino acids) and binding them with all possible methods with respect to a length of a given compound (namely, a size of peptide). It is possible to synthesize a number of chemical compositions through such combinatorial mixing regarding chemical building blocks. For example, systematic combinatorial mixing regarding 100 commutative chemical building blocks consequently produces 100,000,000 tetramer compounds or 10,000,000,000 pentamer compound (see, for example, Gallop et al., J. Med. Chem. (1994) 37 (9): 1233-1250). The preparation and screening of a combinatorial chemical library are well known in a technical field of the art (see, for example, U.S. Pat. Nos. 6,004,617 and 5,985,365). Such a combinatorial chemical library is concerned with peptide libraries (see, for example, U.S. Pat. No. 5,010,175; Furka, (1991) Int. J. Pept. Prot. Res., 37: 487-493; and Houghton et al., (1991) Nature, 354: 84-88), peptoids (see, for example, WO 91/19735), encoded peptides (see, for example, WO 93/20242), random bio-oligomers (see, for example, WO 92/00091), benzodiazepines (see, for example, U.S. Pat. No. 5,288,514), diversomers such as hydantoins, benzoazepines and dipeptides (see, for example, Hobbs, (1993) Proc. Natl. Acad. Sci. USA, 90:6909-6913), vinylogous polypeptides (see, for example, Hagihara, (1992) J. Amer. Chem. Soc., 114: 6568), non-peptidic peptide imitations having a β-D-glucose skeleton (see, for example, Hirschmann, (1992) J. Amer. Chem. Soc., 114: 9217-9218), analogous organic syntheses of low-molecular weight compound libraries (see, for example, Chen, (1994) J. Amer. Chem. Soc., 116: 2661), oligo carbamates (for example, Cho, (1993) Science, 261: 1303), and/or peptidyl phosphonates (see, for example, Campbell, (1994) J. Org. Chem., 59: 658), and so on. Also, nucleic acid libraries (see, for example, Gordon, (1994) J. Med. Chem., 37: 1385), peptide nucleic acid libraries (see, for example, U.S. Pat. No. 5,539,083), antibody libraries (see, for example, Vaughn, (1996) Nature Biotechnology, 14: 309-314), carbohydrate libraries (see, for example, Liang et al., (1996) Science, 274: 1520-1522 and U.S. Pat. No. 5,593,853), isoprenoid libraries as an organic low molecular library (see, for example, U.S. Pat. No. 5,569,588), thiazolidinone and metathiazonone libraries (see U.S. Pat. No. 5,549,974), pyrrolidine libraries (see U.S. Pat. Nos. 5,525,735 and 5,519,134), morpholino compound libraries (see U.S. Pat. No. 5,506,337), benzodiazepine libraries (see U.S. Pat. No. 5,288,514), and the like can be used. Furthermore, commercially available libraries (for example, libraries manufactured by ComGenex Inc., U.S.A., Asinex Ltd., Russia, Tripos, Inc., U.S.A., ChemStar, Ltd., Russia, 3D Pharmaceuticals Inc., U.S.A., and Martek Biosciences Corporation) can be used.

The expression of GTRAP3-18 can be quantitatively determined by, for example, assaying a transcription product (mRNA) of GTRAP3-18 gene. For example, it can be carried out by detecting and assaying the amount of expression of GTRAP3-18 mRNA according to known genetic engineering and molecular biology technologies by procedures known in the field of the art for detecting and assaying the expression of a specified gene, for example, in situ hybridization, northern blotting, dot blot, RNase protection assay, RT-PCR, real-time PCR (Journal of Molecular Endocrinology, 25, 169-193 (2000) and references cited therein), and a DNA array analysis method (Mark Shena ed., Microarray Biochip Technology, Eaton Publishing, 2000).

For example, in the case of a method of detecting the amount of GTRAP3-18 mRNA using an oligonucleotide probe (northern blot analysis method), this method includes at least the following steps:

(a) preparing RNA from a cell having been contacted with a test substance;

(b) electrophoretically separating RNA prepared in the step (a);

(c) hybridizing RNA of the step (b) with an oligonucleotide probe under a stringent condition; and (d) comparing the amount of GTRAP3-18 mRNA with a control cell, by using the amount of label of the oligonucleotide probe as hybridized in RNA in the step (c) as an index of the GTRAP3-18 mRNA.

In comparison with the result of the control cell, the test substance significantly lowering the amount of GTRAP3-18 mRNA is specified as a target substance (substance increasing the amount of intracellular glutathione).

Since the oligonucleotide probe is hybridized with GTRAP3-18 mRNA under a stringent condition (for example, conditions described in JP10-508186A and JP09-511236A), a DNA having precisely complementary with an arbitrary region of mRNA is used. Such a DNA can also be obtained by, for example, cutting GTRAP3-18 cDNA by an appropriate restriction enzyme. Alternatively, such a DNA can be synthesized in vitro according to well known chemical synthesis technologies described in Carruthers, (1982) Cold Spring Harbor Symp. Quant. Biol., 47: 411-418; Adams, (1983) J. Am. Chem. Soc., 105: 661; Belousov, (1997) Nucleic Acid Res., 25: 3440-3444; Frenkel, (1995) Free Radic. Biol. Med., 19: 373-380; Blommers, (1994) Biochemistry, 33: 7886-7896; Narang, (1979) Meth. Enzymol., 68: 90; Brown, (1979) Meth. Enzymol., 68; 109; Beaucage, (1981) Tetra. Lett., 22: 1859; and U.S. Pat. No. 4,458,066.

The oligonucleotide probe is labeled by a radio isotope (RI) method or a non-RI method, and it is preferred to employ a non-RI method. Examples of the non-RI method include a fluorescent labeling, a biotin labeling and a chemiluminescence method, and it is preferred to employ a fluorescent labeling. As a fluorescent substance, ones capable of being bound with a base segment of an oligonucleotide can be properly chosen and used; and cyanine dyes (for example, $Cy_3$ and $Cy_5$ of CyDye™ series), a rhodamine 6G reagent, N-acetoxy-$N^2$-acetylaminofluorene (AAF), AAIF (an iodine derivative of AAF), and the like may be used. For labeling, well known methods in the art (for example, a random prime method, a nick translation method, amplification of DNA by PCR, a labeling/tailing method, and an in vitro transcription method) may be properly chosen and used. For example, a labeled oligonucleotide probe can be prepared by introducing a functional group (for example, a primary aliphatic amino group and an SH group) into an HRF oligonucleotide and binding such a functional group with the foregoing label.

The amount of GTRAP3-18 mRNA can also be assayed by using a DNA microarray. This method includes at least the following steps;
(a) preparing RNA from a cell having been contacted with a test substance;
(b) preparing labeled cDNA from RNA of the step (a);
(c) contacting the labeled cDNA of the step (b) with a DNA microarray; and
(d) comparing the amount of GTRAP3-18 mRNA with a result of a control cell, by using the amount of the labeled cDNA as hybridized in a capture probe of the DNA microarray in the step (c) as an index of the amount of GTRAP3-18 mRNA.

In comparison with the result of the control cell, the test substance significantly lowering the amount of GTRAP3-18 mRNA is specified as a target substance (substance increasing the amount of intracellular glutathione).

Furthermore, the amount of GTRAP3-18 mRNA can also be measured by an RT-PCT method. This method includes at least the following steps:
(a) preparing RNA from a cell having been contacted with a test substance;
(b) synthesizing cDNA from RNA of the step (a); and
(c) comparing the amount of GTRAP3-18 mRNA with a result of a control cell by using the amount of cDNA synthesized in the step (b) as an index of the amount of GTRAP3-18 mRNA.

In comparison with the result of the control cell, the test substance significantly lowering the amount of GTRAP3-18 mRNA is specified as a target substance (substance increasing the amount of intracellular glutathione).

The primer set to be used can be designed by using a commercially available software, for example, Oligo™ (manufactured by National Bioscience Inc., U.S.A.) and GENETYX (manufactured by Software Development Co., Ltd., Japan) on the basis of a known GTRAP3-18 cDNA sequence, and then be synthesized and purified.

Another method of assaying the expression of a GTRAP3-18 gene is to quantitatively determine the amount of a GTRAP3-18 protein, an expression product of the GTRAP3-18 gene. Such quantitative determination of a protein can be carried out according to known genetic engineering and molecular biology technologies known in the art for detecting and assaying the amount of a specified protein, for example, in situ hybridization, western blotting, and various immuno-histochemical methods.

Concretely, using an antibody capable of specifically recognizing GTRAP3-18 protein can carry out the quantitative determination. The antibody is a polyclonal antibody or a monoclonal antibody, and each antibody includes all of an entire molecule capable of binding with an epitope of the GTRAP3-18 protein and Fab, F(ab')$_2$ and Fv fragments. For example, when such an antibody is a polyclonal antibody, it is obtained from a serum after immunizing an animal with the GTRAP3-18 protein or a partial fragment thereof as an immunogen. As the animal, mice, rats, rabbits, goats, chickens, and the like are used.

The monoclonal antibody can be prepared according to a known monoclonal antibody preparation method (Tankuron Kotai (Monoclonal Antibody), Nagamune, Hideaki and Terada, Hiroshi, Hirokawa Bookstore, 1990; and Monoclonal Antibody, James W. Goding, third edition, Academic Press, 1996).

As a labeling substance for an antibody, enzymes, radioactive isotopes or fluorescent dyes can be used. The enzyme is not particularly limited so far as it meets such requirements that it has a large turnover number; that it is stable even upon binding with an antibody; and that it specifically colors a substrate. Enzymes for usual EIA, for example, peroxidase, β-galactosidase, alkaline phosphatase, glucose oxidase, acetylcholine esterase, glucose-6-phosphate dehydrogenase, and malate dehydrogenase can be used. Antienzymatic substances, coenzymes and the like can also be used. Binding of these enzymes with antibody can be carried out by a known method using a crosslinking agent such as maleimide compounds. As the substrate, known substances can be used depending upon the kind of an enzyme to be used. For example, when peroxidase is used as the enzyme, 3,3',5,5'-tetramethylbenzidine can be used, and when alkaline phosphatase is used as the enzyme, para-nitrophenol or the like can be used. As the radioactive isotope, ones which are used in usual RIA, for example, $^{125}$I and $^3$H can be used. As the fluorescent dye, those for usual fluorescent antibody method, for example, fluorescence isothiocyanate (FITC) and tetramethyl rhodamine isothiocyanate (TRITC) can be used.

Such a method using an antibody can be, for example, carried out by immunostaining such as tissue or cell staining; immuno-scanning electron microscopy; immunoassay such as competitive immunoassay or non-competitive immunoassay; radioimmunoassay (RIA), fluorescent immunoassay (FIA), luminescence immunoassay (LIA), enzymatic immunoassay (EIA), ELISA, and the like can be employed; and the assay can be carried out by performing or not performing B-F separation. RIA, EIA, FIA and LIA are preferable; and sandwich type assay is further exemplified. The sandwich type assay may be simultaneous sandwich type assay, forward sandwich type assay or reverse sandwich type assay.

According to the foregoing exemplified methods, it is possible to specify a substance decreasing the amount of the GTRAP3-18 protein in a cell (namely, a substance increasing the amount of intracellular glutathione) while making the expression of the GTRAP3-18 gene as an index.

The substance increasing the amount of intracellular glutathione can also be specified by searching for a substance inhibiting a function of the GTRAP3-18 protein. The function of the GTRAP3-18 protein is, for example, inhibition of the EAAC1 activity. Accordingly, in a cell where GTRAP3-18 and EAAC1 coexist, when the EAAC1 activity (glutamic acid transport) is promoted, it can be judged as its cause that a test substance has inhibited the function of GTRAP3-18. Also, since the promotion of the EAAC1 activity (inhibition of the function of GTRAP3-18) causes an increase in the amount of intracellular glutathione, the inhibition of the function of GTRAP3-18 can also be judged by assaying the amount of glutathione.

As the working examples, experimental results on which the invention of the present application has been based are shown below.

Example 1

Figure 1:
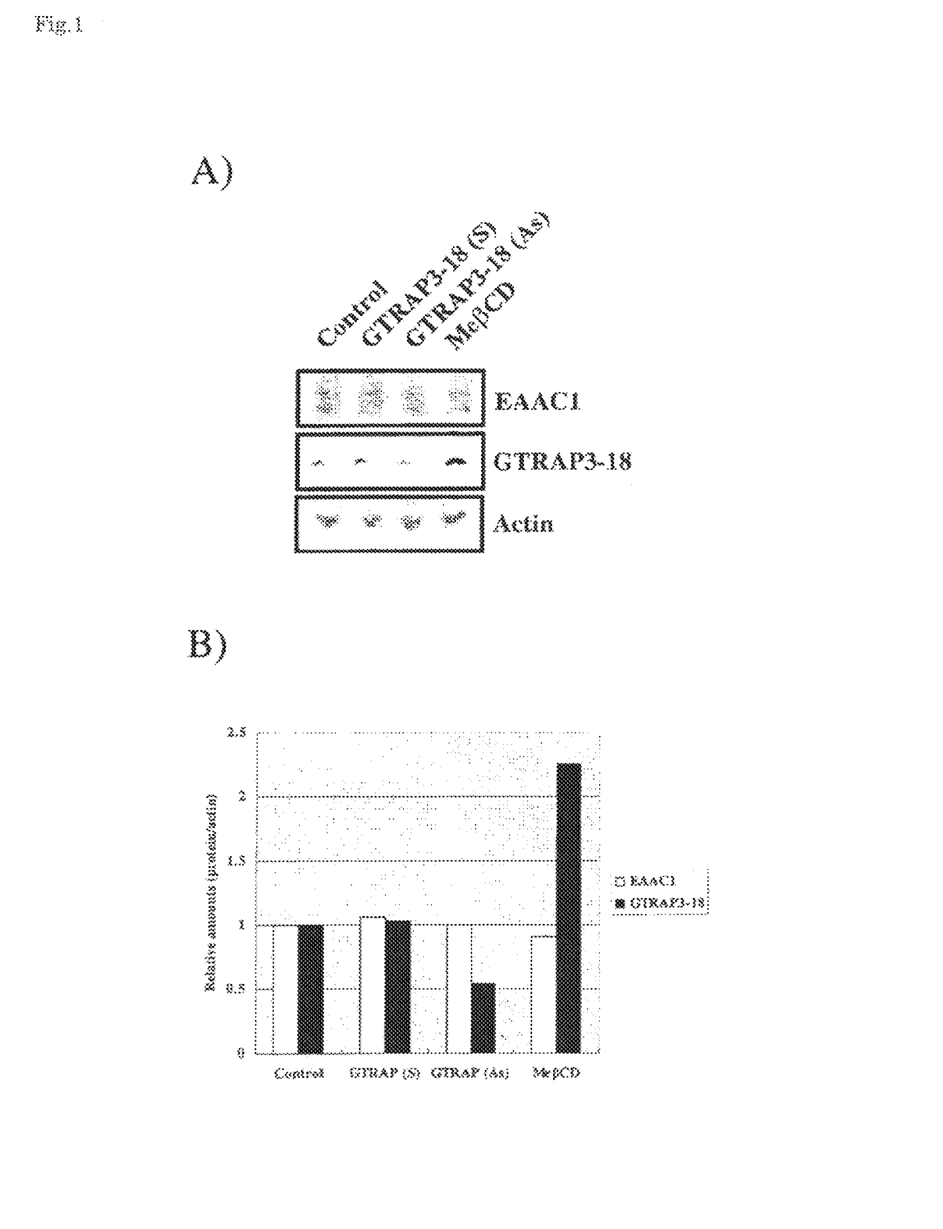
FIG. 1 Results obtained by examining influences of a GTRAP3-18 antisense oligonucleotide and methyl-β-cyclodextrin (MeβCD) against the expression of a GTRAP3-18 protein of an HEK293 cell. A GTRAP3-18 sense oligonucleotide (GTRAP3-18(S)) or an antisense oligonucleotide (GTRAP3-18(As)) was introduced into an HEK293 cell, or 250 μM of methyl-β-cyclodextrin (MeβCD) was made to act thereon. A) After homogenizing the cell, western blot was performed using an anti-EAAC1 antibody, an anti-GTRAP3-18 antibody and an anti-actin antibody. B) The results of the western blot were digitalized and indicated in terms of a ratio to actin. GTRAP3-18 decreased by the introduction of the GTRAP3-18 antisense oligonucleotide, and GTRAP3-18 increased by MeβCD. The amount of EAAC1 did not change.

By transiently introducing an antisense oligonucleotide of GTRAP3-18 into an HEK293 cell, the amount of GTRAP3-18 in the cell was decreased (FIG. 1). Next, the amount of intracellular glutathione was assayed by ThioGlo-1 (manufactured by Calbiochem). An increase of the amount of GTRAP3-18 was confirmed by a western blot method. A cell into which a sense oligonucleotide had been introduced was used as a control group.

Figure 2:
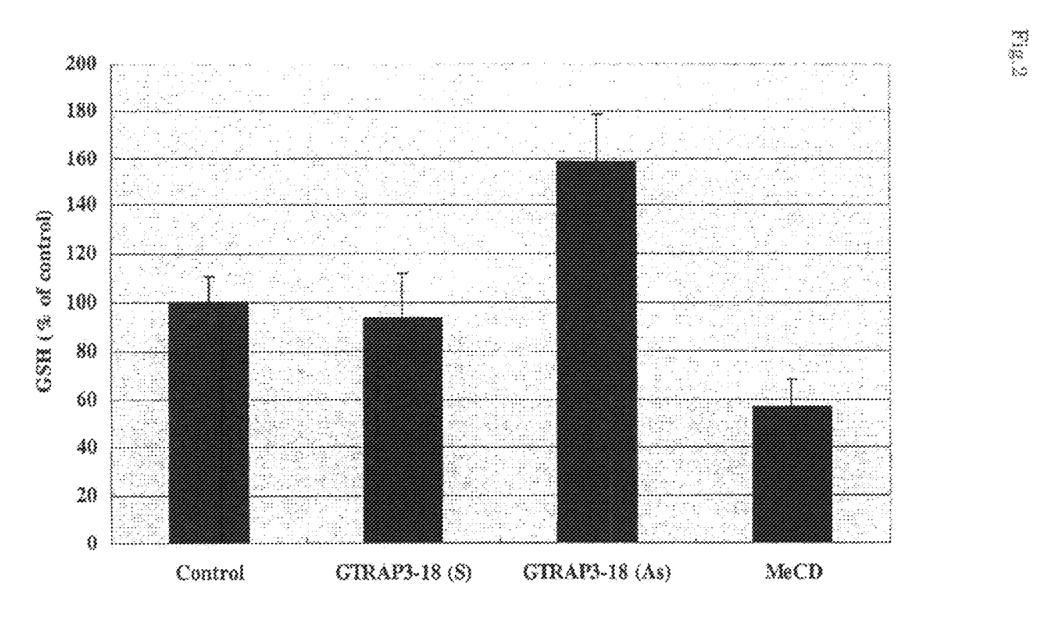
FIG. 2 The amount of intracellular glutathione (GSH) was quantitatively determined under the conditions of FIG. 1. Glutathione increased by the introduction of the GTRAP3-18 antisense oligonucleotide, and glutathione decreased by MeβCD.

As a result, in the cell in which the amount of GTRAP3-18 had been decreased by introducing the antisense oligonucleotide, the amount of glutathione significantly increased as compared with the control group (FIG. 2).

This result demonstrates that it is possible to increase the amount of intracellular glutathione by decreasing the amount of GTRAP3-18.

On the other hand, it was confirmed by a western blot method that when methyl-β-cyclodextrin (MeβCD) was added to HEK293 cell, the amount of GTRAP3-18 increased as compared with the control group (FIG. 1). At that time, the amount of intracellular glutathione significantly decreased as compared with the control group (FIG. 2).

This result demonstrates that the amount of intracellular glutathione decreases by increasing the amount of GTRAP3-18.

From the foregoing results, it has been confirmed that it is possible to search for a substance increasing the amount of intracellular glutathione by using a change in the amount of GTRAP3-18 in the cell (or a change in the function of GTRAP3-18) as an index.

Figure 3:
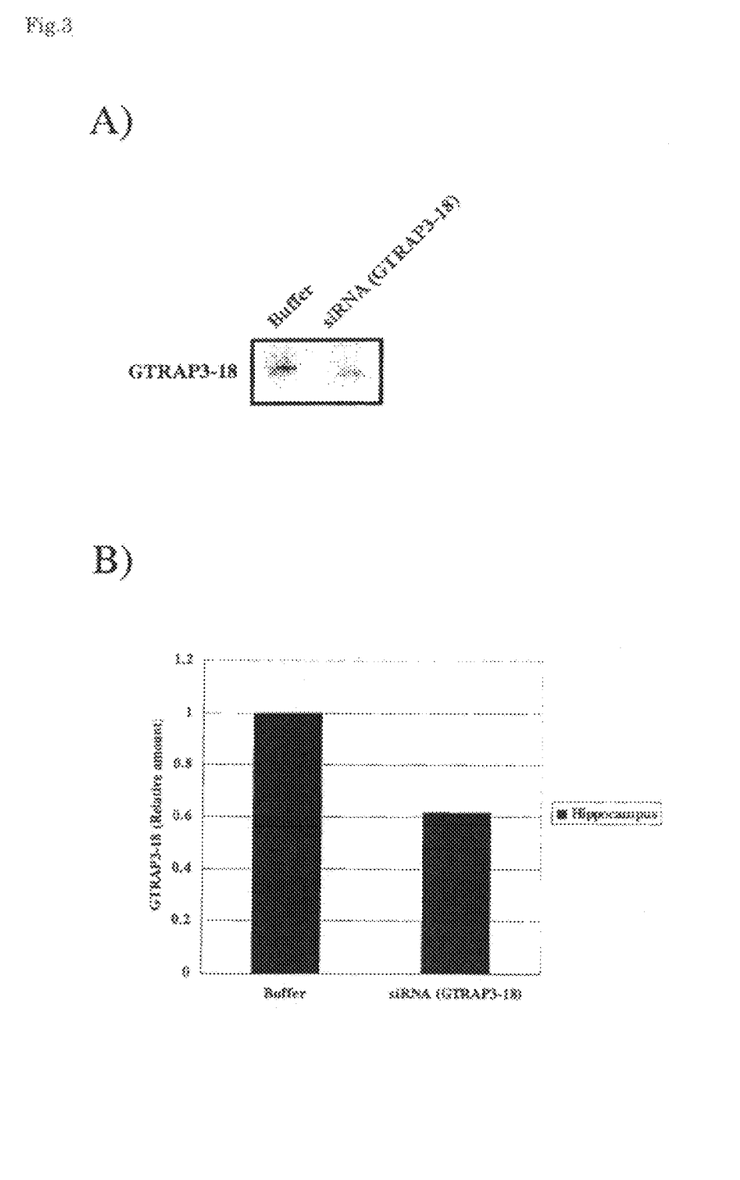
FIG. 3 Results obtained by examining influences of GTRAP3-18 siRNA against the expression of a GTRAP3-18 protein of a mouse hippocampus cell. A) After homogenizing the cell, western blot was performed using an anti-GTRAP3-18 antibody. B) The results of the western blot were digitalized and indicated in terms of a ratio to the buffer administration. The amount of GTRAP3-18 decreased by the introduction of GTRAP3-18 siRNA.
Figure 4:
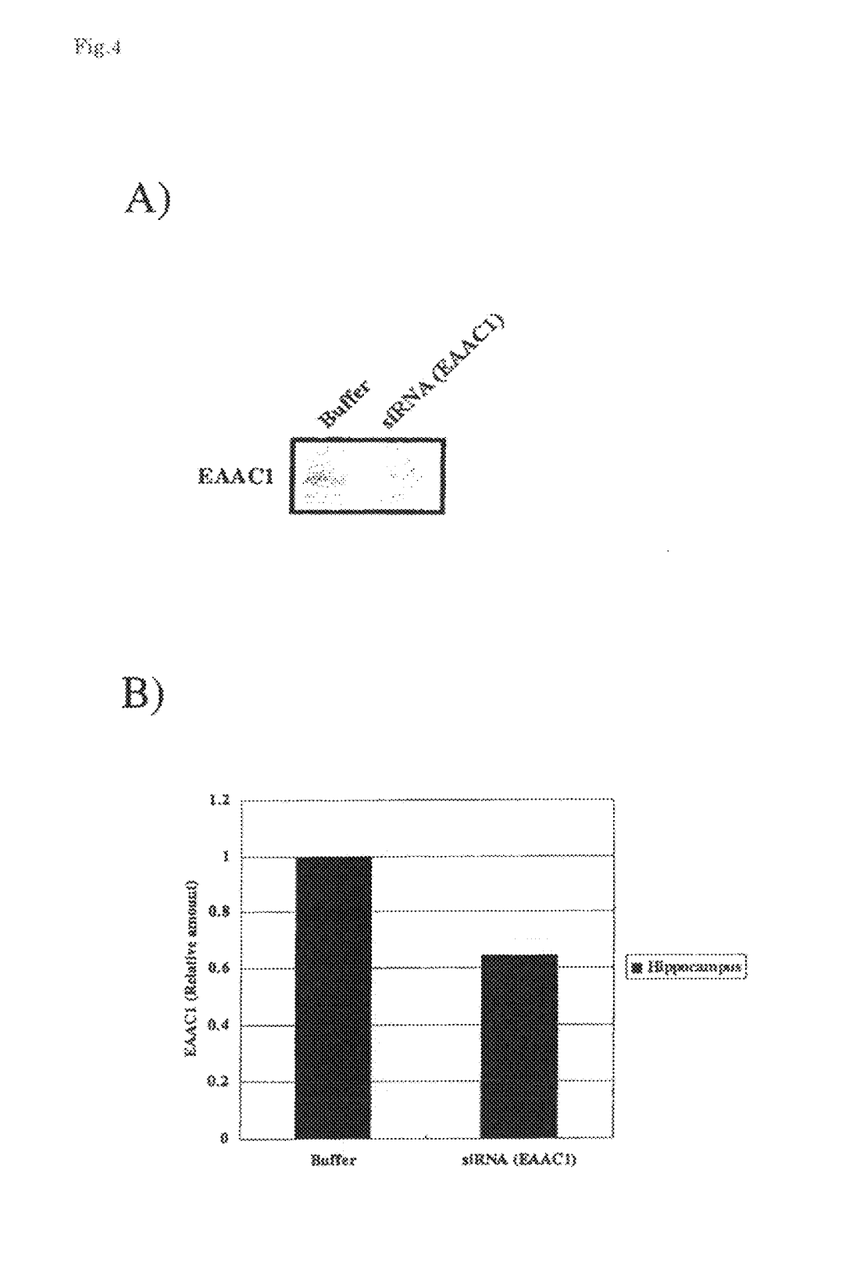
FIG. 4 Results obtained by examining influences of EAAC1 siRNA against the expression of an EAAC1 protein of a mouse hippocampus cell. A) After homogenizing the cell, western blot was performed using an anti-EAAC1 antibody. B) The results of the western blot were digitalized and indicated in terms of a ratio to the buffer administration. The amount of EAAC1 decreased by the introduction of EAAC1 siRNA.

Example 2 siRNA against GTRAP3-18 was administered (10 μg/h) in a cerebral ventricle of a mouse. After one week, the amount of GTRAP3-18 in a hippocampus cell significantly decreased as compared with the case of administering a control (buffer) (FIG. 3). Similarly, in the case of administering siRNA against EAAC1 in a cerebral ventricle of a mouse, the amount of EAAC1 in a hippocampus cell was assayed, and it was confirmed that the amount of EAAC1 significantly decreased by this siRNA (FIG. 4).

Next, after decreasing the amount of GTRAP3-18 or EAAC1 in the hippocampus cell, the amount of glutathione was assayed. That is, an extract from the hippocampus tissue was mixed with a reaction solution containing EDTA (ethylenediaminetetraacetic acid), GSH reductase, DTNB (5,5'-ditiobis-nitrobenzoic acid) and NADPH, and an absorbance at 412 nm was measured. After determining a concentration by using an absorbance of a GSH standard solution, it was corrected by a tissue weight.

Figure 5:
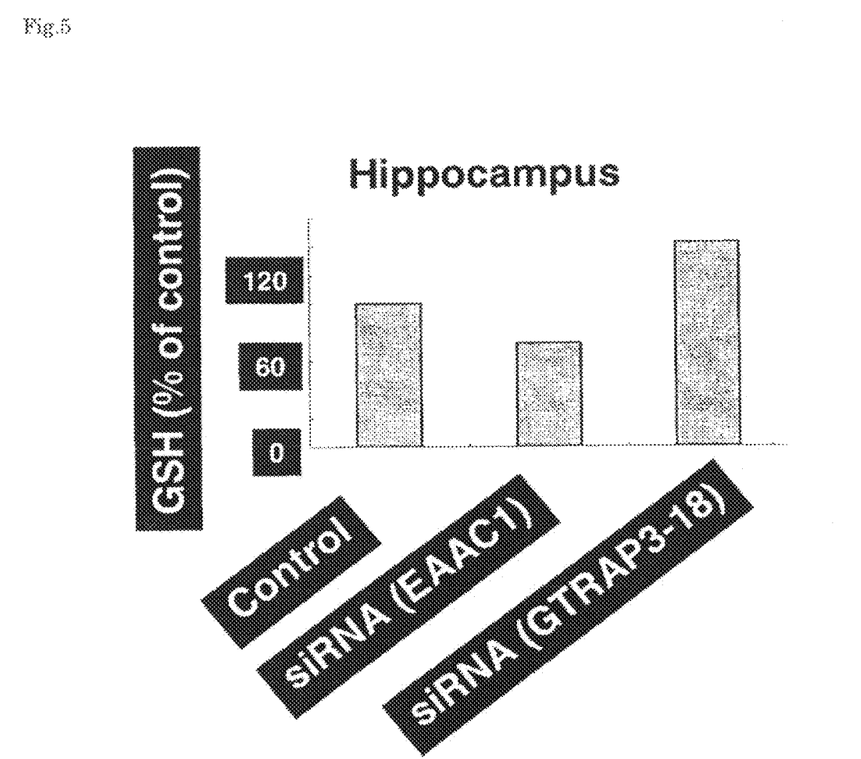
FIG. 5 Results obtained by quantitatively determining the amount of glutathione in hippocampus under the conditions of FIGS. 3 and 4. The amount of glutathione of hippocampus decreased by the intraventricular administration of EAAC1 siRNA, whereas the amount of glutathione increased by GTRAP3-18 siRNA.

As shown in FIG. 5, in the mouse hippocampus cell in which the amount of EAAC1 had been decreased, the amount of the glutathione decreased as compared with the control, whereas in the mouse hippocampus cell in which the amount of GTRAP3-18 had been decreased, the amount of glutathione significantly increased as compared with the control.

Figure 6:
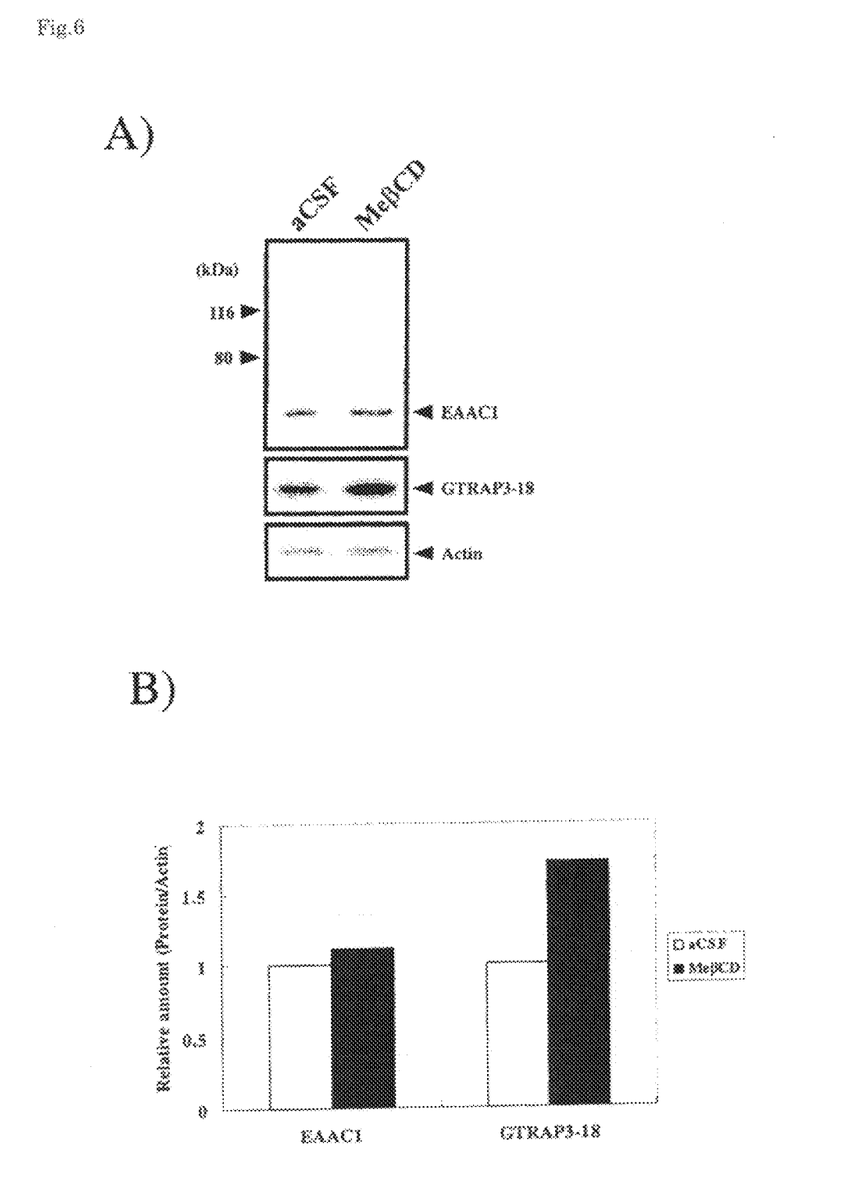
FIG. 6 Results obtained by examining influences of methyl-β-cyclodextrin (MeβCD) against the expression of a GTRAP3-18 protein of mouse hippocampus. A) After homogenizing the cell, western blot was performed using an anti-EAAC1 antibody, an anti-GTRAP3-18 antibody and an anti-actin antibody. B) The results of the western blot were digitalized and indicated in terms of a ratio to actin. GTRAP3-18 increased by MeβCD. The amount of EAAC1 did not change.
Figure 7:
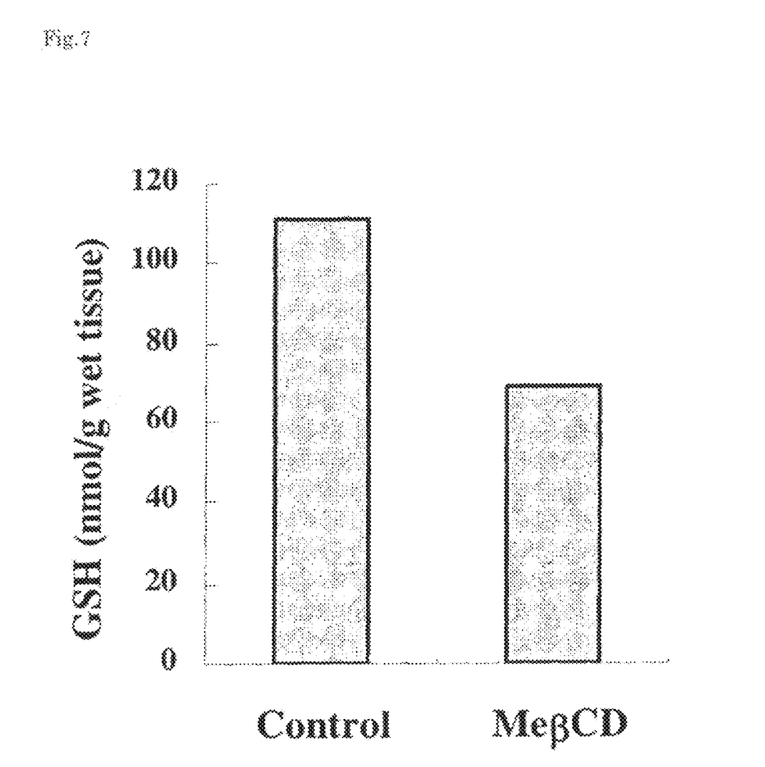
FIG. 7 The amount of intracellular glutathione (GSH) was quantitatively determined under the conditions of FIG. 6. Glutathione decreased by MeβCD.

On the other hand, when methyl-β-cyclodextrin (MeβCD) was administered in a cerebral ventricle of a mouse, the amount of GTRAP3-18 in the hippocampus cell increased as compared with the control group (FIG. 6). At that time, the amount of glutathione in the hippocampus cell significantly decreased as compared with the control group (FIG. 7).

From these results, it has been confirmed that even a cell in an animal body, screening of a substance increasing the amount of glutathione is possible by using an effect against the expression of GTRAP3-18 as an index.

The invention claimed is:

1. A method for screening a substance increasing the amount of neuronal glutathione, which comprises contacting a test substance with a neuronal cell expressing a GTRAP3-18 protein, and specifying as a target substance a substance which decreases the amount of expression of the GTRAP3-18 protein or inhibits a function of the GTRAP3-18 protein, thereby increasing the amount of glutathione in the neuronal cell.

2. The method according to claim 1, wherein the neuronal cell is in an animal body.

* * * * *